United States Patent
Fadaei et al.

(10) Patent No.: US 10,241,102 B2
(45) Date of Patent: Mar. 26, 2019

(54) SYSTEM AND METHOD FOR DETERMINING PROPERTIES OF AN OIL MATERIAL

(71) Applicant: THE GOVERNING COUNCIL OF THE UNIVERSITY OF TORONTO, Toronto (CA)

(72) Inventors: Hossein Fadaei, Calgary (CA); Matthew David Ooms, Toronto (CA); David Allan Sinton, Toronto (CA)

(73) Assignees: Hossein Fadaei, Calgary (CA); Matthew David Ooms, Toronto (CA); David Allan Sinton, Toronto (CA)

( * ) Notice: Subject to any disclaimer, the term of this patent is extended or adjusted under 35 U.S.C. 154(b) by 191 days.

(21) Appl. No.: 15/043,644

(22) Filed: Feb. 15, 2016

(65) Prior Publication Data
US 2016/0238526 A1 Aug. 18, 2016

Related U.S. Application Data

(60) Provisional application No. 62/115,907, filed on Feb. 13, 2015.

(51) Int. Cl.
*G01N 21/41* (2006.01)
*G01N 33/28* (2006.01)
*G01N 21/552* (2014.01)

(52) U.S. Cl.
CPC ....... *G01N 33/2823* (2013.01); *G01N 21/553* (2013.01)

(58) Field of Classification Search
CPC .. G01N 21/553; G01N 33/2823; G01N 33/28; G01N 33/2835; G01N 33/2829; G01N 33/2888

(Continued)

(56) References Cited

U.S. PATENT DOCUMENTS 5,266,800 A * 11/1993 Mullins ................ G01N 21/359
250/253
5,828,458 A * 10/1998 Taylor .................. G01N 21/532
356/440

(Continued)

FOREIGN PATENT DOCUMENTS

EP 2799867 A1 * 11/2014 ............ B60W 10/06

OTHER PUBLICATIONS

Zhou et al., Lasing action in strongly coupled plasmonic nanocavity arrays, Nature Nanotechnology, Jul. 2013, vol. 8, pp. 506-511, Macmillan Publishers Limited.

(Continued)

*Primary Examiner* — Hina F Ayub
*Assistant Examiner* — Amanda Merlino
(74) *Attorney, Agent, or Firm* — Norton Rose Fulbright Canada LLP

(57) ABSTRACT

Systems and methods for classifying oil materials. A method of determining a refractive index of oil comprising: generating an incident beam, incident on a conductive material and at an angle of incidence to the conductive layer, between the conductive material and an oil material; monitoring the power of a reflected beam; and determining an angle of resonance by changing the angle of incidence of the incident beam; determining a refractive index of the oil material using at least the power of the reflected beam. Systems and methods may be provided for on-surface testing or downhole in situ testing.

39 Claims, 15 Drawing Sheets

(58) Field of Classification Search
USPC .......................................... 356/70, 134–135
See application file for complete search history.

(56) References Cited

U.S. PATENT DOCUMENTS

| | | | | |
|---|---|---|---|---|
| 6,731,388 | B1* | 5/2004 | Simon | G01N 21/553 356/445 |
| 8,358,419 | B2* | 1/2013 | Walters | G01N 21/553 257/443 |
| 2010/0241362 | A1* | 9/2010 | Yoshikawa | G01N 21/553 702/24 |
| 2015/0233823 | A1* | 8/2015 | Echtermeyer | G01N 21/554 356/445 |
| 2017/0067826 | A1* | 3/2017 | Sadowski | G01N 21/553 |

OTHER PUBLICATIONS

BP, BP Statistical Review of World Energy 2013; BP: London, U.K., 2012.

Chaudhuri, Fundamentals of Petroleum and Petrochemical Engineering, 2011, pp. 25-48, CRC Press: Boca Raton, FL, 2011.

Giles et al., Crude Oils: Their Sampling, Analysis, and Evaluation, 2010, pp. 1-3 and 9-13, ASTM International: West Conshohocken, PA.

Riazi, et al., Use of the Refractive Index in the Estimation of Thermophysical Properties of Hydrocarbons and Petroleum Mixtures, Industrial & Engineering Chemistry Research, 2001, vol. 40, pp. 1975-1984, ACS Publications.

Taylor et al., Refractive index measurements of diluted bitumen solutions, Fuel, 2001, vol. 80, pp. 2013-2018, Elsevier Science Ltd.

Buckley, et al., Crude oil and asphaltene characterization for prediction of wetting alteration, Journal of Petroleum Science and Engineering, 2002, vol. 33, pp. 195-202, Elsevier Science B.V.

Den Boer et al., Measurement of the complex refractive index of liquids in the infrared using spectroscopic attenuated total reflection ellipsometry: correction for depolarization by scattering, Applied Optics, Sep. 1, 1995, vol. 34, No. 25, pp. 5708-5714.

Gateau, et al., Heavy Oil Dilution, Oil & Gas Science and Technology—Rev. IFP, 2004, vol. 59, No. 5, pp. 503-509, Institut français du pétrole.

Castillo, et al., Measurement of the Refractive Index of Crude Oil and Asphaltene Solutions: Onset Flocculation Determination, Energy Fuels, 2010, 24, pp. 492-495, American Chemical Society.

Wang, et al. Fiber-Optic Chemical Sensors and Biosensors, Institute of Analytical Chemistry, Chemo- and Biosensors, University of Regensburg, 2013, 85, pp. 487-508, American Chemical Society, Regensburg, Germany.

Hoa, et al., Towards integrated and sensitive surface plasmon resonance biosensors: A review of recent progress, Biosens, Biosensors and Bioelectronics, 2007, 23, pp. 151-160, Elsevier B.V.

Tong, et al., Recent Advances in Plasmonic Sensors, Sensors 2014, 14, pp. 7959-7973, MDPI, Basel, Switzerland.

Luchansky, et al., High-Q Optical Sensors for Chemical and Biological Analysis, Anal. Chem. 2011, 84, pp. 793-821, American Chemical Society.

Kawata, et al., Plasmonics for near-field nano-imaging and superlensing, Nature Photonics 2009, vol. 3, pp. 388-394, Macmillan Publishers Limited.

Mubeen Et al., On the Plasmonic Photovoltaic, ACS Nano 2014, 8, pp. 6066-6073.

Dickerson, et al., Gold nanorod assisted near-infrared plasmonic photothermal therapy (PPTT) of squamous cell carcinoma in mice, Cancer Letters, 2008, 269, pp. 57-66, Elsevier Ltd.

Jain, et al., Noble Metals on the Nanoscale: Optical and Photothermal Properties and Some Applications in Imaging, Sensing, Biology, and Medicine, Accounts of Chemical Research, Dec. 2008, vol. 41, No. 12, pp. 1578-1586, American Chemical Society.

Torkamani, et al., Plasmon-enhanced microalgal growth in miniphotobioreactors, Applied Physics Letters, 2010, 97, 043703, American Institute of Physics.

Ooms, et al., Culturing photosynthetic bacteria through surface plasmon resonance, Applied Physics Letters, 2012, 101, 253701, American Institute of Physics.

Samsonoff, et al., A photosynthetic-plasmonic-voltaic cell: Excitation of photosynthetic bacteria and current collection through a plasmonic substrate, Applied Physics Letters, 2014, 104, 043704, AIP Publishing.

Hecht, Optics, 4th ed., 2002, pp. 122-131, Addison-Wesley: Reading, MA.

Escobedo, et al., Optofluidic Concentration: Plasmonic Nanostructure as Concentrator and Sensor, Nano Lett. 2012, 12, pp. 1592-1596, American Chemical Society.

Nooke, Gas Detection by Means of Surface Plasmon Resonance Enhanced Ellipsometry, Technischen Universitat Berlin: Berlin, Germany, 2012.

Aguirre, et al., Development of a Surface Plasmon Resonance n-dodecane Vapor Sensor, Sensors, 2007, 10, pp. 1954-1961, MDPI.

Kretschmann et al., Radiative Decay of Non Radiative Surface Plasmons Excited by Light, Zeitschrift für Naturforschung A, 1968, vol. 23a, pp. 2135-2136.

Mullins, et al., The Electronic Absorption Edge of Petroleum, Applied Spectroscopy, 1992, vol. 46, No. 9, pp. 1405-1411, Society for Applied Spectroscopy.

Kurihara, et al., Assymetric SPR sensor response curve-fitting for the accurate determination of the SPR resonance angle, Sensors and Actuators B, 2002, 86, pp. 49-57, Elsevier Science B.V.

Zhao et al., Interplay between the Physical Properties of Athabasca Bitumen+Diluent Mixtures and Coke Deposition on a Commercial Hydroprocessing Catalyst, Energy Fuels, 2008, 22, pp. 1747-1758, American Chemical Society.

Homola, et al., Surface Plasmon Resonance (SPR) Sensors, Springer Series on Chemical Sensors and Biosensors, 2006, vol. 4, pp. 45-67, Springer-Verlag Berlin Heidelberg.

Novotny et al., Principles of Nano-Optics, 1st ed., 2006, pp. 363-416, Cambridge University Press: Cambridge, U.K.

Palik, Handbook of Optical Constants of Solids; 1998, pp. 313-335, Academic Press: New York.

Bauch et al., Plasmon-Enhanced Fluorescence Biosensors: a Review, Plasmonics, 2013, pp. 11-13, Springer Science+Business Media New York.

* cited by examiner

| | |
|---|---|
| 1 | $P = \dfrac{RT}{V-b} - \dfrac{a}{T^{0.5}V(V-b)}$ |
| 2 | $a = 0.42748R^2T_c^{2.5}/P_c$ |
| 3 | $b_{RK} = 0.08664RT_c/P_c$ |
| 4 | $b = \beta b_{RK}$ |
| 5 | $\dfrac{1}{\beta} = 1 + \{0.02[1 - 0.92\exp(-1000|T_r - 1|)] - 0.035(T_r - 1)\}(r - 1)$ |
| 6 | $r = R_m/R_{m,ref}$ |
| 7 | $R_m = ML_w/d_w$ |
| 8 | $r = \dfrac{n^2 - 1}{n^2 + 1}$ |

| | |
|---|---|
| $P$ | Pressure |
| $T$ | Temperature |
| $V$ | Volume |
| $R$ | Gas constant |
| $b$ | EOS parameter |
| $\alpha$ | EOS parameter |
| $b_{RK}$ | Parameter |
| $T_r$ | Reduced temperature |
| $T_c$ | Critical temperature |
| $P_c$ | Critical pressure |
| $R_{xs}$ | Molar refraction |
| $R_{xs,ref}$ | Molar refraction of a reference fluid (i.e. methane) |
| $L$ | Refractive index parameter |
| $d_{20}$ | Density at 20 °C |
| $n$ | Refractive index |

FIG. 16

SYSTEM AND METHOD FOR DETERMINING PROPERTIES OF AN OIL MATERIAL

CROSS REFERENCE

This application is a non-provisional of and claims all benefit to, including priority of, U.S. Application No. 62/115,907 filed Feb. 13, 2015, incorporated herein by reference.

FIELD

Some embodiments described herein relate generally to oil and gas analysis, and more particularly to systems and methods for measuring refractive index of an oil material.

BACKGROUND

The measurement of the physicochemical and thermophysical properties of crude oil and related hydrocarbons (fractions) may be relevant in the oil and gas industry. Fluid properties may play a role in facility design, well completion, surface production facilities, managing reservoir recovery, production forecasting, and downstream refining and/or processing.

Analysis of hydrocarbon fluids, however, may be associated with high pressure and temperature conditions, complex mixtures and opaqueness of the material.

The opaqueness of crude oils, specially medium and heavy oils, may be an issue for light based characterization techniques (e.g., due to absorption).

In addition, for sampling/analysis of downhole and surface flow lines, the multiphase (water, oil and gas) nature of the flow may have further complications. Measurement of fluid properties therefore may require measurement methods robust to these conditions.

A new, improved and/or alternate solution is provided.

SUMMARY

The present disclosure relates to a system and method for measuring the refractive index of an oil material.

In an aspect, a method of determining a refractive index of oil may be provided, including: generating an incident beam, incident on a conductive material and at an angle of incidence to the conductive layer, between the conductive material and an oil material; monitoring the power of a reflected beam; and determining a refractive index of the oil material using at least the power of the reflected beam.

In another aspect, an apparatus for determining a refractive index of an oil material may be provided, including: a light source for generating an incident beam; an optically permissive material, for refracting the incident beam; a conductive material; and a detector configured for sensing characteristics of a reflected beam; wherein the oil material is co-operatively disposed relative to the conductive material and the oil material interacts with the conductive material such that when the incident beam interacts with the conductive material under resonant conditions, the detector senses an attenuation in the power of the reflected beam.

In another aspect a method of generating electromagnetic radiation characteristic data associated with an oil material may be provided, the method including: positioning a sample in relation to a conductive material such that, when an incident beam of electromagnetic radiation is received by the conductive material, the sample absorbs at least a fraction of the energy of the received electromagnetic radiation; directing an incident beam of electromagnetic radiation into a permissive material having a refractive index greater than the refractive index of the oil material, such that the incident beam of electromagnetic radiation is directed onto the conductive material such that at least a fraction of the energy of the beam of electromagnetic radiation is reflected by the conductive material; and sensing an intensity of the reflected beam of electromagnetic radiation such that electromagnetic radiation characteristic data is generated.

In another aspect, a method of determining a refractive index of oil is provided, including placing an interrogation face of a transparent body having a first indicia of refraction into contact with an oil material, the interrogation face having a plasmon surface resonance coating exposed to the oil material, generating an incident beam into the transparent body and internally reflecting it against an interrogation face to generate an output beam exiting the transparent body; monitoring the power of the output beam; and determining a refractive index of the oil material using at least the power of the reflected beam.

In another aspect, the conductive material is a thin conductive film.

In another aspect, the conductive material is a thin gold film.

In another aspect, the conductive material is deposited in the Kretschmann configuration.

In another aspect, a laser diode module generates the incident beam.

In another aspect, the laser diode module is a polarized 4.5 mW laser diode module.

In another aspect, the changing of the angle of incidence is conducted using one or more micrometer adjusted rotation arms.

In another aspect, the angle of incidence is adjusted in increments of approximately 0.2 degrees.

In another aspect, the angle of incidence is adjusted in increments of approximately 0.04 degrees.

In another aspect, the angle of incidence is adjusted in increments of approximately 0.2 degrees to identify regions of interest, and adjusted in increments of approximately 0.04 degrees in regions of interest.

In another aspect, the method further comprises determining one or more other thermophysical values, including at least one of oil type and quality.

In another aspect, the method further comprises classifying the oil material using at least the refractive index of the oil material.

In another aspect, the classifying of the oil material includes determining the ratio of solvent and crude oil.

In another aspect, the solvent includes toluene.

In another aspect, the oil quality includes one or more API gravity values.

In another aspect, the method is used in a downhole environment.

In another aspect, the method is used in an on-surface testing environment.

In another aspect, the classifying of the oil material includes detecting fluid, oil, gas and brine phases.

In another aspect, the classifying of the oil material includes detecting asphaltene content.

In another aspect, the classifying of the oil material includes detecting emulsions when combined with a microchip.

In another aspect, the refractive index is determined using at least one of the angle of resonance; the refractive index of a prism coupled with the conductive layer and the oil material; and the thickness of the conductive layer.

In another aspect, the wavelength of the incident beam is in the infrared region.

In another aspect, the incident beam traverses through a prism made of materials having a refractive index of at least the refractive index of the oil material.

In another aspect, the incident beam traverses through a prism made of a material having a refractive index of at least about 1.5.

In another aspect, the conductive layer is between approximately 50 nm thick.

In another aspect, a pinhole aperture is used to select a central part of the beam to aid in reducing diverging portions of the beam.

In various further aspects, the disclosure provides corresponding systems and devices, and logic structures such as machine-executable coded instruction sets for implementing such systems, devices, and methods.

In this respect, before explaining at least one embodiment in detail, it is to be understood that some embodiments are not limited in application to the details of construction and to the arrangements of the components set forth in the following description or illustrated in the drawings. There may be embodiments capable of being practiced and carried out in various ways. Also, it is to be understood that the phraseology and terminology employed herein are for the purpose of description and should not be regarded as limiting.

BRIEF DESCRIPTION OF THE DRAWINGS

In the drawings, embodiments of the invention are illustrated by way of example. It is to be expressly understood that the description and drawings are only for the purpose of illustration and as an aid to understanding, and are not intended as a definition of the limits of the invention.

Embodiments will now be described, by way of example only, with reference to the attached figures, wherein:

FIG. 15 provides a table of equations that may be applied in determining various parameters.

FIG. 16 is a table of variables that may be used in the equations of FIG. 15 and their descriptions.

DETAILED DESCRIPTION

Figures 1, 2:
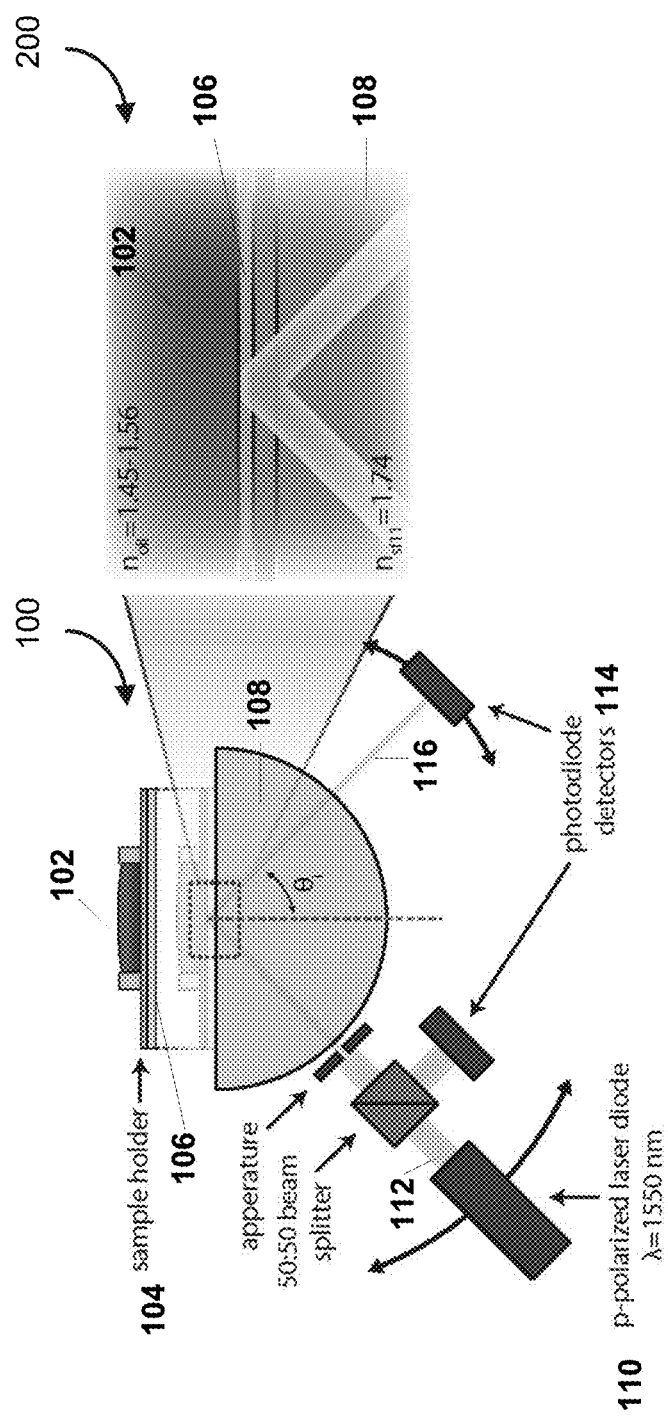
FIG. 1 illustrates a device for SPR based determination of the refractive index of an oil material, according to some embodiments.
FIG. 2 illustrates a magnified portion of FIG. 1, according to some embodiments.

Preferred embodiments of methods, systems, and apparatus suitable for measuring the refractive index of a sample of an oil material are described through reference to the drawings.

A sample of an oil material's refractive index can be used to characterize and estimate its thermo-physical properties such as density, viscosity, pressure, critical constants and heat capacity and thus the refractive index may be a property of significant interest to reservoir engineers. A conventional refractometer, based on light transmission, can be used for transparent and semi-transparent fluids, but is not suitable for opaque liquids such as heavy and extra heavy crude oils. For example, various aspects of the composition of an oil material may be characterized, such as solvent compositions (e.g., solvent ratio), density, oil type, oil color, solubility, etc.

An approach to deal with the issue of opaque fluids is to dilute the crude oil with solvents (e.g., toluene), measure the refractive index of the diluted mixtures and extrapolate the refractive index for the undiluted sample using mixing rules. This approach may not be practical and/or desirable, however, for continuous refractive index measurement (e.g., inline) where dilution adds another complication to the measurement procedure. One considered way to accommodate dark heavy crude oils are reflection based techniques using a fiber optic or critical angle measurement. In both approaches, the absorption of the fluid can be an issue when measuring samples with high absorption (dark oils) at the applied wavelength, thus a correction for absorption may be needed for refractive index measurement.

Surface plasmon resonance (SPR) based techniques may be utilized to determine a refractive index of an oil material. Features of SPR based techniques which may be particularly useful in this context include non-intrusiveness and amenability to in-line measurements.

There may be high sensitivity obtainable when employing SPR-based techniques, and detection may not require any dilution for heavy and extra-heavy oils, potentially providing a non-intrusive and reliable approach to oil characterization well suited to laboratory applications and/or continuous measurement/monitoring both for downhole and on-surface applications. The accurate determination of the refractive index of an oil material may be of significant value as various other thermophysical values can be deduced, which may potentially provide insight into oil material type and quality. In some embodiments, classifying of the oil material includes detecting emulsions when combined with a microchip.

Classifying different types of oil material by measuring refractive index may also be of interest to assess quality and composition changes during different stages of the recovery process. The methods and systems described may, in some embodiments, present tools to distinguish between a wide range of different oil material types without requiring any pre-treatment or dilution.

The systems and methods may also be utilized for other analyses, such as detecting fluid, oil, gas and brine phases, or detecting asphaltene content.

A potential advantage of using SPR based techniques in the context of oil material measurements may be the surface confined nature of the measurement; since the resonance is sensitive only to the oil material within a few hundred nanometers of the sensor surface, impurities and sediments that exist in the bulk are less likely to impact the signal once the surface of the sensor may be wetted with oil material.

Some embodiments may include the use of various structural elements, such as small-scale channels (e.g., micro and/or nano-scale channels) that are used to determine additional properties of the oil material and/or to analyze only components of the oil material in the small-scale channels (e.g., to filter a particular phase of an oil material, or to filter out impurities/sediment/silt that may otherwise impact the accuracy of the analysis of the oil material). Various optical properties of the oil material may change depending on the structural geometry of the conductive surface which can affect the wetting properties of the surface and consequently the phase that is in contact with the sensor.

Additionally, other fields related to the oil and gas industry could potentially benefit from such a measurement approach, including the measurement of asphaltene deposition onset detection, emulsion detection in general and particularly in the oil transport lines, and contamination detection in the gas flow lines.

The oil material may be positioned substantially adjacent to a conductive surface (e.g. gold or any other suitable material), upon which an emitted beam (e.g. light, laser, various electromagnetic emissions) may be configured to be incident on. For the purposes of this description, the emitted beam generated at a source may be referred to as the incident beam.

An emitted beam (e.g. light, laser, various electromagnetic emissions), when incident on a conductive surface (e.g. metal), may interact with the conduction electrons of the conductive surface and the energy may be absorbed, reflected, and/or transmitted.

A potentially important consideration may be the selection of a suitable wavelength where the oil material is only marginally absorbing, such as wavelengths in the infrared region. For example, 1550 nm may be selected as a wavelength of an incident beam, as it represents a region of the spectrum where oil material may be weakly absorbing. There may be a range of wavelengths where this occurs (for example, an oil material absorption spectrum may be provided in the figures of U.S. Pat. No. 5,266,800). A potential that arises with absorption is optical loss and degraded signal, because light is being coupled into the oil material rather than the conductive surface.

In some embodiments, the conductive surface may be coupled with a prism, which may have various associated properties (e.g. refractive index, thickness, geometry). The prism, in some embodiments, may be configured for operation in high-pressure environments, such as a downhole environment.

When the wavelength and frequency of the incident beam may be matched with the natural frequency and momentum of the conduction electrons, resonant conditions may arise and the conduction electrons may begin to oscillate as a group, forming a plasmon. The particular wavelength and/or the angle of the incident beam and/or the refractive index of a conductive layer (e.g., gold) and/or prism may also be a factor in determining when resonant conditions arise.

Under these resonant conditions, a portion of the energy of the incident beam may be coupled into these electron oscillations and a decrease in the intensity of the reflected beam can be observed by a detector, such as a photodetector.

The angle at which resonance occurs may depend upon: (a) the thickness of the conductive surface, (b) the refractive index of the coupling prism and (c) the refractive index of the oil material. The knowledge of any three of the parameters (angle of resonance, the thickness of the conductive layer, the refractive index of the coupling prism, and the refractive index of the material) may allow the accurate estimation of the fourth parameter using theoretical models. In some embodiments, there may be an additional step of calibrating the apparatus to solve for various coefficients and/or parameters using, for example, oil materials of known refractive index or angle of resonance.

In some embodiments, the angle of incidence of the incident beam may be adjustable. As the angle of incidence of the incident beam is adjusted, a detector may be configured to detect the intensity of the reflected beam. The profile of the intensity of the reflected beam may reflect various optical phenomena, such as the formation of plasmons. Where the power of the reflected beam is minimized, there may be indications that plasmons may be being formed and the angle of incidence may be an angle in which resonance occurs (the angle of resonance).

At specific angles of incidence of the incident beam, greater than the critical angle for total internal reflection to occur, the tangential components of the beam's electric field may match the resonant conditions of the free electrons in the conductive layer. Under these conditions, energy is transferred from the incident beam into the electrons, causing them to oscillate.

The angle at which the minimum reflectance occurs (the angle of resonance, $\theta_{spr}$) may indicate coupling of the incident beam into surface plasmon modes of the conductive surface.

The maximum point of each curve may occur at the angle where the incident beam transitions from refraction to total internal reflection. At this point, the largest amount of incident light is reflected back to the detector. As the incident angle increases and the resonant conditions are approached, the light begins to couple into surface plasmons in the conductive layer and the reflected power drops quickly, until $\theta_{spr}$ is reached. The resonance conditions may be sensitive to the refractive index of both the oil material and the coupling prism.

The angle of resonance, $\theta_{spr}$ when coupled with knowledge of the wavelength of the incident beam, the geometry of the conductive layer and the refractive index of the surrounding materials, may be used to determine the refractive index of the oil material.

The refractive index of the oil material may be indicative of various physicochemical and thermo-physical properties of the oil material, and may be used, for example, to differentiate various oil materials by oil types (e.g., from light oil to extra heavy oil and bitumen) and/or by oil material mixtures (oil/solvent mixtures, etc.). For example, a common issue encountered in oil and gas recovery processes may be the determination of the ratio of solvent and crude oil in production lines, as a solvent may often be used to increase the mobility of in-situ oil deposits to facilitate recovery.

Various types of identification methods may be utilized to associate refractive indices to types of oil, for example, the use of look up tables, the combination of the refractive indicies with other collected information about the oil material, etc.

Referring to FIG. 1, FIG. 1 illustrates an example embodiment of a device 100 for SPR based determination of the refractive index of an oil material, according to some embodiments. The device 100 has an oil material 102, a sample holder 104, a conductive surface 106, a prism 108, a beam source 110 generating an incident beam 112, detector means 114. The detector means 114 being configured for detecting a reflected beam 116.

In particular, FIG. 1 illustrates a device 100 setup based on incident angle interrogation (Kretschmann configuration). The hemispherical prism 108 (SF11 glass, refractive index 1.74) may be configured such that the incident light contacts the material at a same or similar location for different angles of incidence.

FIG. 2 provides a magnified example of FIG. 1, depicting the interface between the prism 108, the conductive surface 106, and the oil material 102.

In some embodiments, the device 100 may include a glass substrate coated to act as a conductive surface 106 (e.g. with a 30 or a 50 nm gold film), with the oil material 102 interfacing with the top of the prism 108.

In some embodiments, the device 100 may be configured for measurement of the resonance angle based on SPR techniques.

The device 100 may be configured for testing in a variety of environments, such as in laboratory, with isolated materials, and/or in downhole in situ environments. Where the device 100 may be configured for downhole in situ experiments, the device 100 may be utilized in conjunction with other types of apparatus to position the device 100 downhole and/or to retrieve oil materials 102 for use with the device. In some embodiments, the conductive surface 106 (e.g., gold) could be deposited directly onto the prism, eliminating the need for a sample holder 104. A sample holder 104 may be convenient in a lab setting, but down hole it may be unnecessary. In some embodiments, sample holder 104 may be a receptacle adapted for obtaining, positioning, and/or affixing a sample of oil material such that the oil material may be analyzed through the application of an incident beam.

The detector 114 may be one or more photodiodes and/or may be configured to detect the power of a beam generated by beam source 110, the incident beam 112, and/or the reflected beam 116.

The oil material 102 may vary depending on the particular type of experiment, and may be various types of oil and/or mixtures of oils with other substances, such as solvents and/or water. For example, the oil material could be bitumen, oils from various wells, oils mixed with varying ratios of solvent (e.g. toluene), etc. In some embodiments, the oil material 102 may not necessarily be oil, and may be other fluids and/or substances, such as water, drilling fluids, muds, etc. For example, these substances may be used during the drilling process, may be provided from reservoir fluids, etc.

Various characteristics of the apparatus may be important in the determination of the refractive index of the oil material 102, as resonance may be sensitive to the characteristics such as the properties of the sample holder 104, the geometry of the conductive surface 106, the thickness of the conductive surface 106, the geometry of the surrounding materials, the wavelength of the incident beam 112, the angle of incidence of the incident beam 112, the refractive index of the surrounding materials (such as the prism 108), among others.

For example, the prism 108 may be configured with a high refractive index material to increase the range of oil refractive indices that the device 100 can detect. The refractive index of the prism may place a limit on the maximum refractive index of oil that can be detected—a high refractive index prism may mean that the device 100 can detect high refractive index oils such as Athabasca bitumen. In some embodiments, the prism 108 may instead by a transparent body.

In some embodiments, for example, the device 100 may be placed in a shrouded room to limit parasitic radiation.

In some embodiments, for example, the device 100 may be configured for use in the Kretschmann configuration, and in other embodiments, the device 100 may be configured for use in the Otto configuration. Other configurations may also be contemplated.

In some embodiments, for example, the sample holder 104 may include a substrate (such as a rectangular glass substrate having the characteristics SF11 n=1.745 at 1550 nm, 25 mm×25 mm×1 mm) attached to an aluminum cavity with cap to prevent sample evaporation during testing. The substrate may be prepared through, for example, the thermal evaporation of a 2.5 nm chromium adhesion layer followed by the depositing of a conductive surface 106 of 30 nm of gold onto the glass substrate. The sample holder 104 may hold a sample (e.g. 2 mL) of the oil material 102, in contact with a conductive surface 106.

In some embodiments, for example, the conductive surface 106 can be made of various conductive materials, with various geometries and/or thickness. There may be more than one layer. For example, some embodiments may include the use of metal (or metal alloy) thin-films, including those made of gold at a thickness of approximately 30 nm. In some embodiments, the conductive surface 106 may instead be an interrogation face and/or a conductive layer.

Thin layers may be potentially useful to reduce attenuation of light within the conductive surface 106, ensuring efficient energy transfer to the surface charges at the conductive layer-oil interface, but not so thin that the energy transferred into the surface plasmons is simply coupled back out into the prism 108.

In some embodiments, the conductive surface 106 may also incorporate one or more small scale channels (e.g., micro and/or nano channels) which may be used to determine various properties of the oil material. For example, the sizing of the channels may be important in determining what components of the oil material may be affected by the incident beam.

In some embodiments, the channels may be used to separate out components of the oil materials having different phases, as the channels may be sized such that the channels are selective. Measurements may be conducted, for example, on different phases of the oil material through the selection and use of suitably sized channels. The measurements, for example, may be used to separate different phases (oil, water and gas) prior to detection, and multiple SPR sensors may be used in conjunction.

In some embodiments, the channels may be used to separate out impurities, such as silt, sediment, etc., from the oil material for analysis. The channel may include one or more nano-pores that may be used for analysis.

In some further embodiments, the conductive surface 106 may contain both small scale channels and flat surfaces, and analysis on channels and the surfaces may be conducted such that a comparison may be made between the data received from both analyses.

In some embodiments, for example, the prism 108 can be made of various materials, which may have optical properties, such as various refractive indices, and may be configured with various geometries (for example, a hemispherical prism 108 using SF-11 glass may be used). In further embodiments, for conducting analysis of some oil materials 102, which typically have refractive indices between 1.45 and 1.56, a prism 108 is required with refractive index at least greater than approximately 1.56.

Further, in some embodiments, for example, the refractive index of the coupling prism 108 may be greater than that of the material in order to achieve total internal reflection. For example, at $\lambda=1550$ nm, SF-11 glass has a refractive index of 1.74, which may help ensure that total internal reflection could be achieved for oil materials 102.

In some embodiments, for example, the incident beam 112 can be various types of electromagnetic radiation, such as visible light, laser light, etc., with varying power, wavelength, polarization, and configured in various ways. For example, a polarized 4.5 mW laser diode module (e.g. a Thorlabs™, LDM1550) having a wavelength of 1550 nm.

While various wavelengths of the incident beam 112 may be utilized, in some embodiments, infrared wavelengths, such as 1550 nm, may be selected because of the low absorption of oil at these wavelengths. At infrared wavelengths, oils and their constituent components may exhibit low absorption in oil, and therefore, infrared wavelengths may be used in some embodiments in order to limit attenuation of the light through absorption by the oil material 102.

In further embodiments, for example, the incident beam 112 may also be passed through an aperture to select only the central region of the beam and reduce beam divergence.

In some embodiments, for example, the detector can be various types of photodiode detectors, such as a Thorlabs™ S122C.

In some embodiments, for example, the generator of the incident beam 112 and the photodiode detector may be mounted on adjustment means to cause the changing of the angle of incidence, such as, micrometer adjusted rotation arms focused on the radial center of a hemispherical prism 108. There may be other adjustment means to similarly cause the movement of the detector to receive the reflected beam 116.

In this example, the rotation arms may be configured to rotate the generator of the incident beam 112 and to similarly rotate the detector to receive the reflected beam 116.

In some embodiments, for example, the adjustment means may be configured to cause the rotation of the incident beam 112 such that the power of the reflected beam 116 could be measured for various angles of interest. In further embodiments, the adjustment means may be configured such that sweeping the angle of the incident beam 112 across a range was conducted multiple times for each oil material 102 studied, and measured at various angular increments. In further embodiments, the angle increments may be measured at various levels of granularity, in particular, in regions of interest, such as regions around an angle of resonance. For example, the power of the reflected beam 116 may be measured at angle increments of 0.2 degrees, but increments of 0.04 degrees in the region of interest, for greater resolution.

Figure 3:
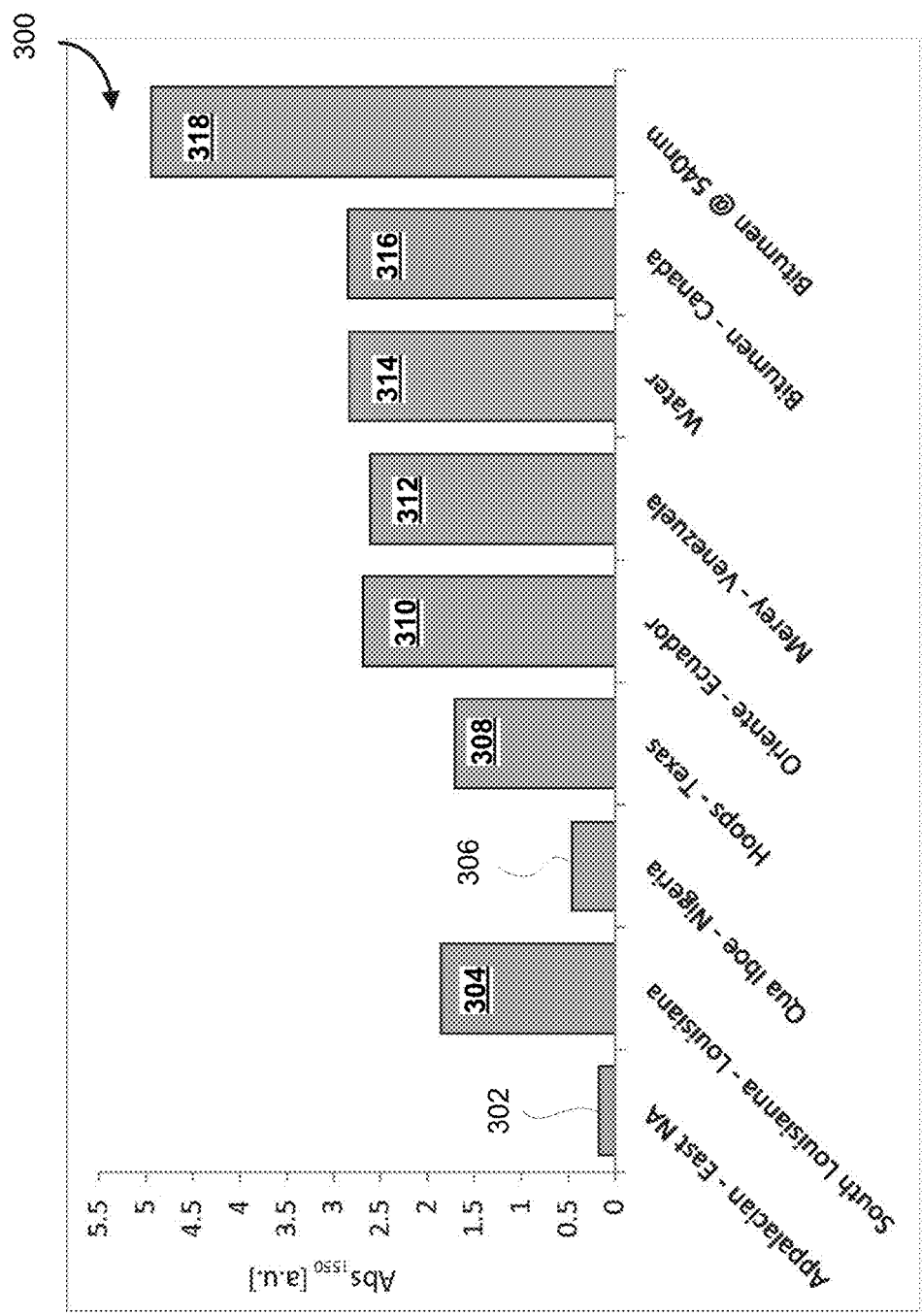
FIG. 3 provides a graph indicating results of absorption (a.u.) at a wavelength of 1550 nm compared over various types of oil materials and/or substances, ranging from water to bitumen, according to some embodiments.

Referring to FIG. 3, FIG. 3 provides a graph 300 indicating experimental results of absorption (Au) compared over various types of oil material, ranging from water to bitumen, according to some embodiments. The bar corresponding to 302 refers to a sample from the Appalachians, 304 refers to a sample from Louisiana, 306 refers to a sample from Nigeria, 308 refers to a sample from Texas, 310 refers to a sample from Ecuador, 312 refers to a sample from Venezuela, 314 is a reference example of water, 316 is a sample from Canada (bitumen), and 318 is a sample of bitumen at 540 nm.

FIG. 3, through graph 300, shows the measured absorption of the oils tested at 1550 nm, and also shows bitumen at a visible wavelength (540 nm) showing that the light is attenuated nearly two orders of magnitude more than at 1550 nm (Absorption ~5 compared to 3 represents that light intensity that makes it through the sample at 540 nm is 100× less than at 1550 nm).

In a study, results were obtained for the analysis of oil material 102 with specific gravities ranging from 0.825 to 1.007 (40 to 9.0° API). The material had undergone two extraction processes: warm-water extraction and naphtha dilution. The naphtha was then recovered by distillation between 151 and 623 K. The Athabasca bitumen (as received with no further treatment) was used for the hydrocarbon phase.

Some properties of the Athabasca bitumen used in the study are presented in Table 1:

TABLE 1

| Properties of Athabasca Bitumen Used in This Study | |
|---|---|
| property | value |
| density (kg/m$^3$) @ 294 | 1026 |
| viscosity (Pa · s) @ 294 | ~2000 |
| SARA fractions (wt %) | |
| saturate | 16.1 |
| aromatic | 48.5 |
| resin | 16.8 |
| asphaltenes (C5) | 18.6 |

Mixtures of Athabasca bitumen and toluene were prepared by dissolving the appropriate ratio (volume based) of the bitumen in reagent grade toluene (99.5% purity, Sigma Aldrich). The mixtures were kept in sealed vials at room temperature to prevent any evaporation prior to testing.

The sample holder 104 and sensor included a rectangular glass substrate (SF11 n=1.745 at 1550 nm, 25 mm×25 mm×1 mm, Newlight Photonics) attached to an aluminum cavity with a cap to prevent material evaporation during testing. The plasmonic substrate (e.g., the sample holder 104 with a conductive surface 106 disposed on it) was prepared by thermal evaporation of a 2.5 nm chromium adhesion layer followed by 30 nm of gold onto the glass substrate. Other types of methods for depositing layers on to a substrate may be utilized.

In the experiment, ~2 mL crude oil (oil-solvent mixture) was placed in the sample holder 104, in contact with the gold side of the glass and the cap was closed.

Light was coupled into surface plasmon modes using the Kretschmann configuration. The apparatus was placed in a shrouded room to limit parasitic radiation. The sample holder 104 cavity was placed in optical contact with the top face of a SF11 glass hemispherical prism 108 (radius 35 mm thickness 20 mm, Newlight Photonics) using an index matched immersion fluid (Cargille Labs, 1815X).

The light source used for interrogation was a polarized 4.5 mW laser diode module (Thorlabs, LDM1550) with $\lambda$=1550 nm. This wavelength was selected because of the low absorption of oil at this wavelength, and other suitable wavelengths may be utilized. The beam from this laser was passed through an aperture to select only the central region of the beam and reduce beam divergence. After reflecting off the glass/gold/oil interface, the reflected beam 116 power was measured using a photodiode detector (Thorlabs, S122C).

The polarization of the light may be an important consideration. In some embodiments, the light may be p-polarized (e.g., the electric field is be perpendicular to the surface). This can be accomplished by using a polarized light source (such as the laser in this study) or by including polarizers in the beam path.

Potentially, the absence of a polarizer may result in a damped SPR signal because all the s-polarized light would be reflected, partially washing out the signal.

The laser source and photodiode detector (Thorlabs, S122C) were mounted on micrometer adjusted rotation arms and focused on the radial center of the hemispherical prism 108, allowing for angle interrogation of the material. As the laser source arm was rotated, the detector arm was similarly rotated to intercept the reflected beam 116 until the maximum reflected power reading for that particular input angle was obtained.

Interrogation proceeded in this way for all angles of interest. The angle sweep was conducted three times for each oil material 102 studied. Before each test, the cavity was cleaned using toluene to remove the oil from the previous test, and then the cavity was rinsed with toluene/isopropanol/water in different cycles to ensure a clean gold surface. The cavity may be dried with air prior to the test. For each material, the reflectance was measured at angle increments of 0.2 degrees. Near the angle of resonance, the reflectance was measured three more times with increments of 0.04 degrees for greater resolution in this region of interest.

In order to measure the refractive index of oil materials 102, infra-red light from a laser diode module ($\lambda$=1550 nm) was coupled with a SF-11 hemispherical prism 108 (Newlight Photonics).

At $\lambda$=1550 nm, SF-11 glass has a refractive index of 1.74, helping ensure that total internal reflection could be achieved for oil materials 102. Light with a wavelength of 1550 nm was used in order to limit attenuation of the light through absorption by the oil material 102. At this wavelength, oils and their constituent components exhibited low absorption.

To test the applicability of this sensor configuration to measuring solvent concentration in heavy oil, samples of Athabasca bitumen were diluted with toluene in ratios from 10 to 90 (v/v).

The refractive index of these dilutions was assumed to be a linear combination of the refractive index of toluene (1.47—supplier provided) and bitumen (1.55—measured) weighted by their volume proportion in the dilution.

Figure 4:
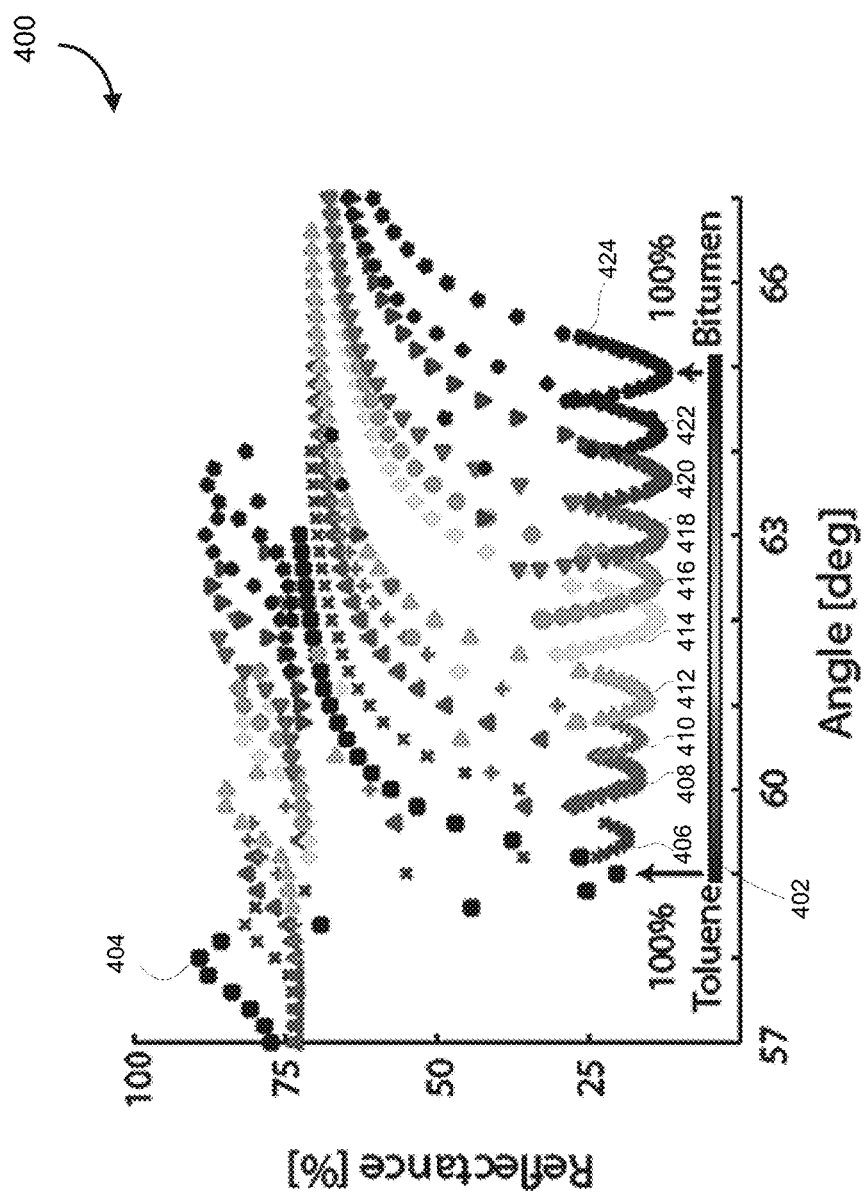
FIG. 4 provides an X-Y graph illustrating resonance angle measurements for Athabasca bitumen and its mixtures with different toluene volume fractions, with the Y axis indicating reflectance [%], and the X axis indicating the angle (degrees) of the incident beam, with the different types and colors of symbols denoting different types of oil, according to some embodiments.

Referring to FIG. 4, FIG. 4 provides an X-Y graph 400 illustrating resonance angle measurements for Athabasca bitumen and its mixtures with different toluene mass fractions, with the Y axis indicating reflectance [%], and the X axis indicating the angle (degrees) of the incident beam, with the different types and colours of symbols denoting different types of oil, according to some embodiments (as shown on bar 402). 404, 406, 408, 410, 412, 414, 416, 418, 420, 422, and 424 are groups of measurements corresponding to various mixtures having different toluene mass fractions; the groups of measurements range from 100% toluene (measurements 404), and 100% bitumen (measurements 424).

FIG. 4 illustrates the resulting reflectance curves for each of the dilutions of oil and shows the response to the dilutions of oil.

Figure 5:
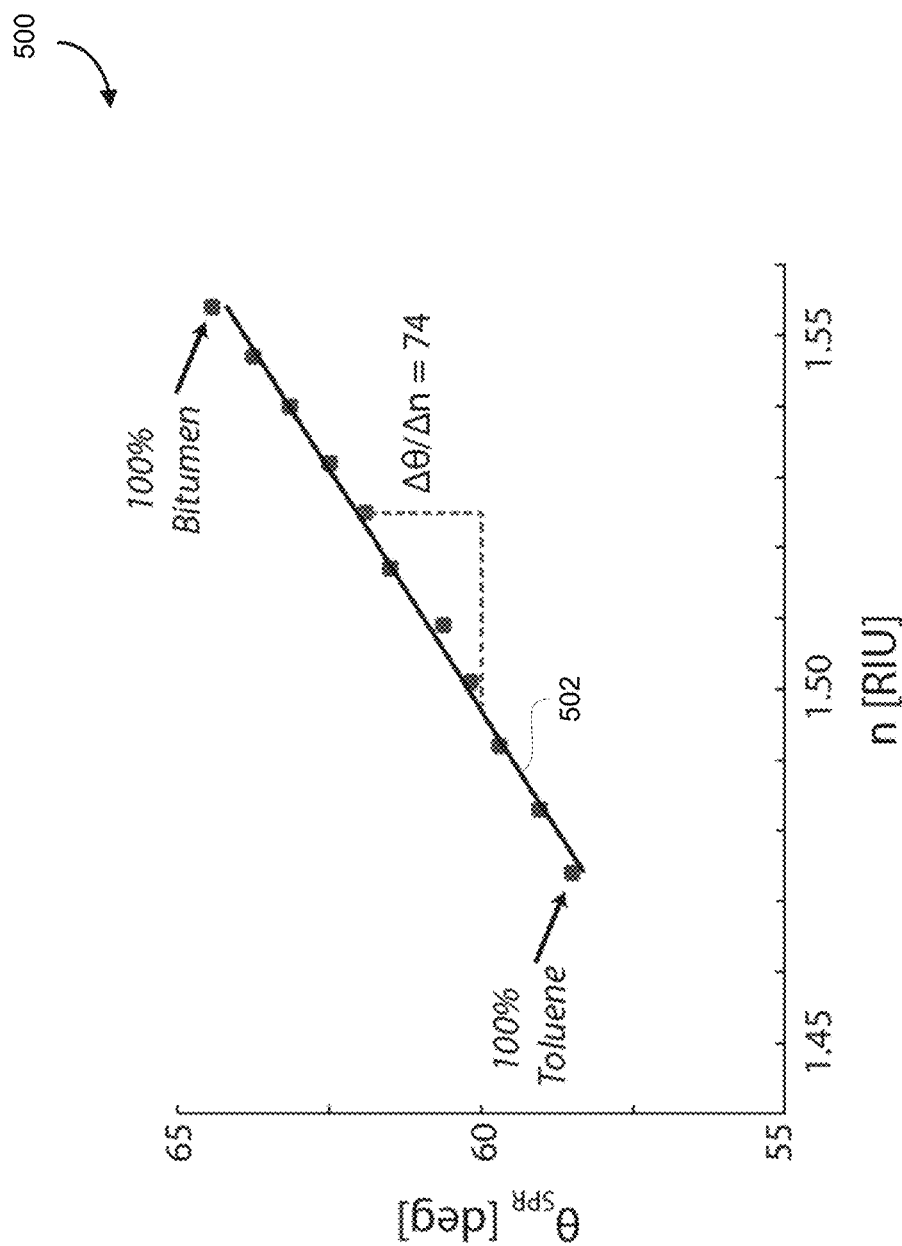
FIG. 5 provides a line graph of the calculated refractive index of the mixtures, and also the corresponding empirical relation for the refractive indices of the mixtures, according to some embodiments.

Referring to FIG. 5, FIG. 5 provides a line graph 500 of the calculated refractive index of the mixtures and also the corresponding empirical relation for the refractive indices of the mixtures, according to some embodiments. The X axis is indicative of the refractive index (in refractive index units), and the Y axis is indicative of the angle of resonance (in degrees). For example, in respect of FIG. 5, the angle of resonance is determined for an oil material, and the relationship between the refractive index and the angle of resonance may be used to determine the refractive index. The data point may be mapped against the line shown in FIG. 5 to determine where on the line (or curve) of best fit 502 the point belongs to between the various ratios of toluene and bitumen (which, for example, may have been derived from experiments or theoretical data). The position of where on the line of the best 502 the data for the oil material belongs may be helpful and/or indicative of the solvent ratio contained within the oil material.

FIG. 5 shows that for each oil dilution, the refractive index and the SPR angle (the minimum point from the curves in FIG. 4), there is a roughly linear relationship between the refractive index and the angle of resonance.

Figure 8:
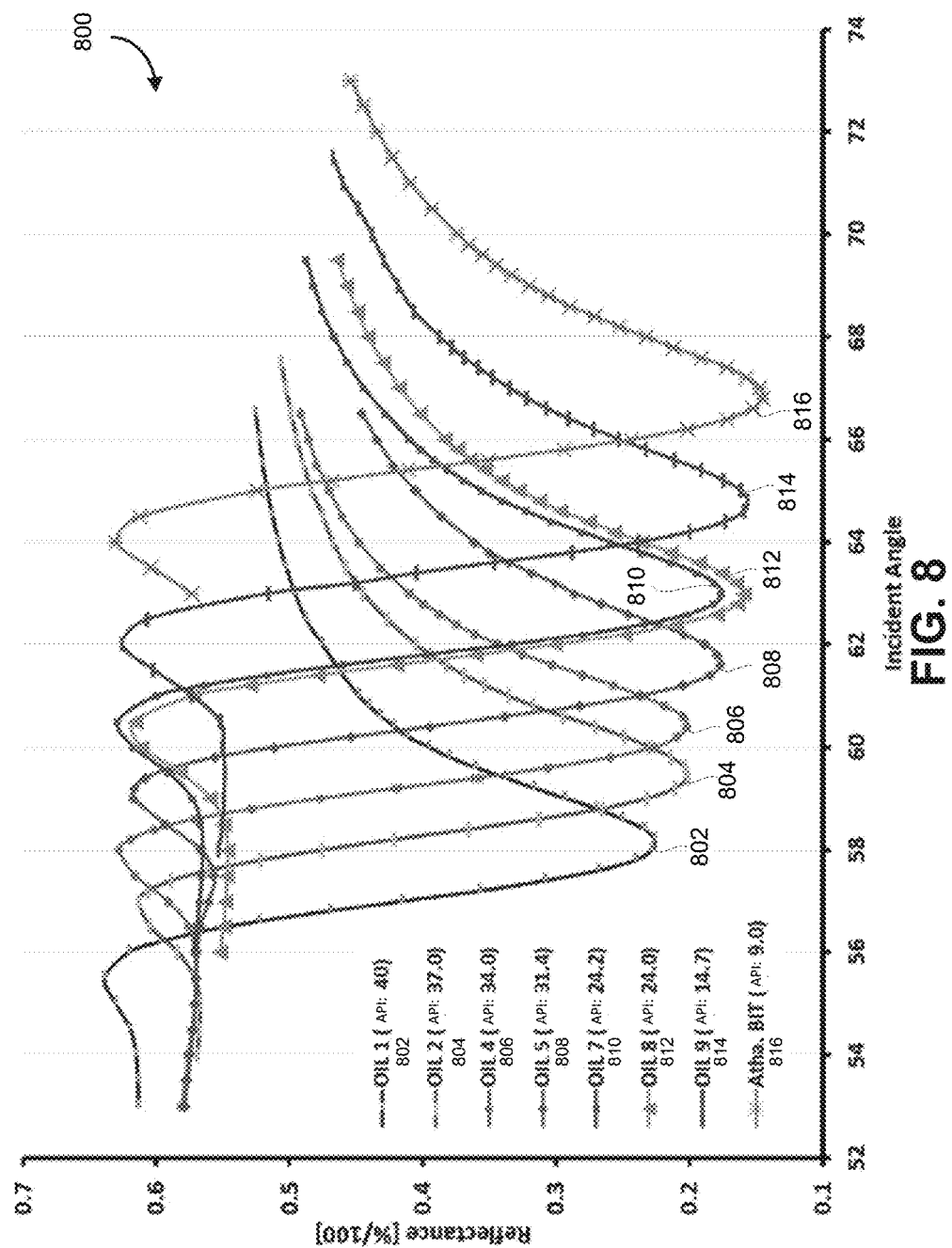
FIG. 8 provides another chart indicating experimental results taken with regards to a set of oil materials having different types of oil, according to some embodiments.

Referring to FIG. 8, FIG. 8 provides a X-Y graph 800 showing the experimental data of incident angle versus the reflectance for a variety of oil materials 102 from around the world, with densities ranging from 0.825 g/cm$^3$ to 1.026 g/cm$^3$ for Athabasca bitumen, ranging from Saudi Arabian light oil (40 API) to Athabasca bitumen of Canada (10 API), according to some embodiments. The X axis may be indicative of the angle of the incident beam, and the Y axis may be indicative of the reflectance (%). The types of oil may be indicated in Table 2, below.

TABLE 2

Oil Material Types

| Sample Number | Oil Type and Region | API |
| --- | --- | --- |
| Oil 1 802 | Appalachian - East NA | 40.0 |
| Oil 2 804 | South Louisiana - Louisiana | 37.0 |
| Oil 3 806 | Qua Iboe - Nigeria | 34.0 |
| Oil 4 808 | Hoops - Texas | 31.4 |
| Oil 5 810 | Vasconia - Columbia | 24.2 |
| Oil 6 812 | Oriente - Ecuador | 24.0 |
| Oil 7 814 | Merey - Venezuela | 14.7 |
| Oil 8 816 | Bitumen - Canada | 6.4 |

Curves were fitted to the data in order to determine the $\theta_{spr}$ for each oil material sample described in Table 2. $\theta_{spr}$ for each material is plotted against the refractive index of the oil in FIG. 6.

Figure 6:
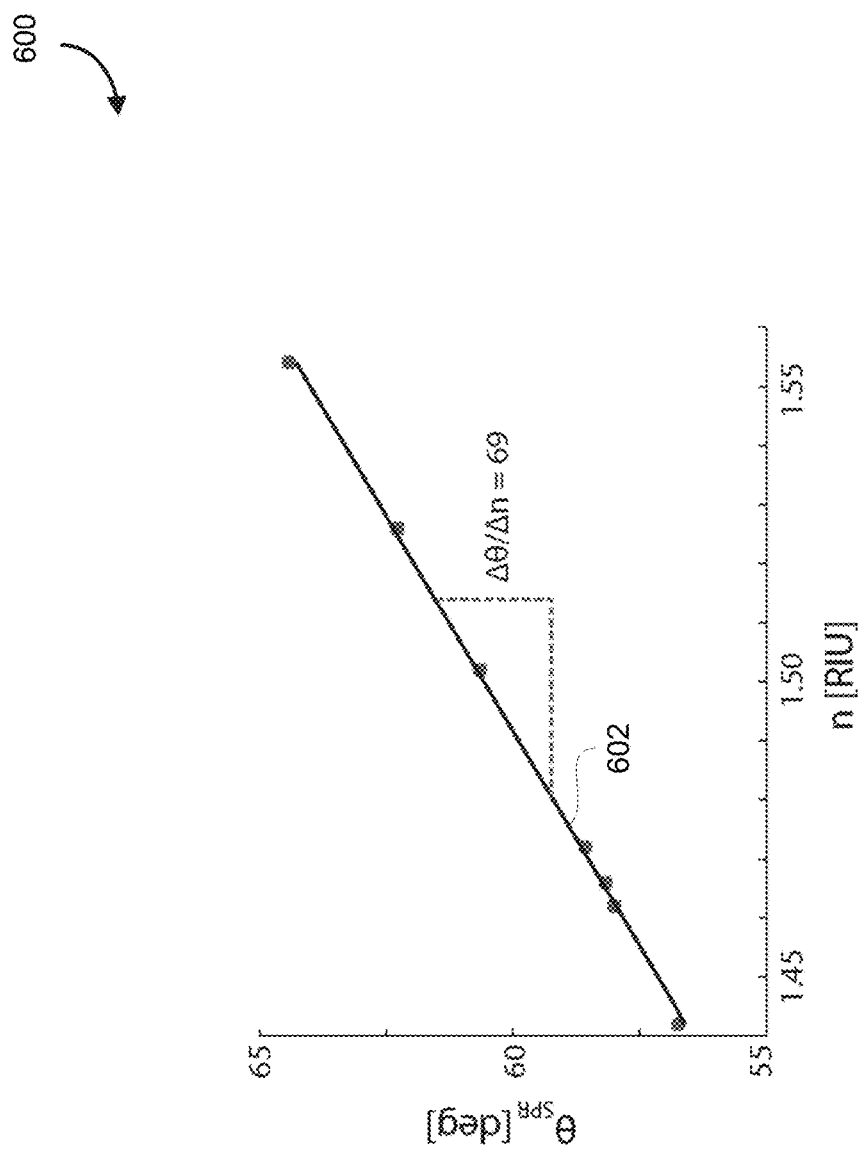
FIG. 6 provides an X-Y graph where the angle of resonance and refractive index is plotted for each material, with X axis indicating the refractive index n, in refractive index units, and the Y axis indicating the angle of resonance, in degrees, according to some embodiments.

Referring to FIG. 6, FIG. 6 provides an X-Y graph 600 where the angle of resonance and refractive index is plotted, with X axis indicating the refractive index n, in refractive index units, and the Y axis indicating the angle of resonance, according to some embodiments.

Over the range of refractive indices represented by the oil materials 102, a nearly linear response of $\theta_{spr}$ with respect to refractive index was observed with a slope ($\Delta\theta/\Delta n$) of 69. A line of best fit is provided at 602.

It is interesting to note the difference between the $\Delta\theta/\Delta n$ for the dilutions and oil materials 102 as shown in FIG. 4 and FIG. 6 respectively. While for small variations in refractive index the change in $\theta_{spr}$ is nearly linear, for larger changes this linearity breaks down, which is typical of SPR based sensors.

Figure 7:
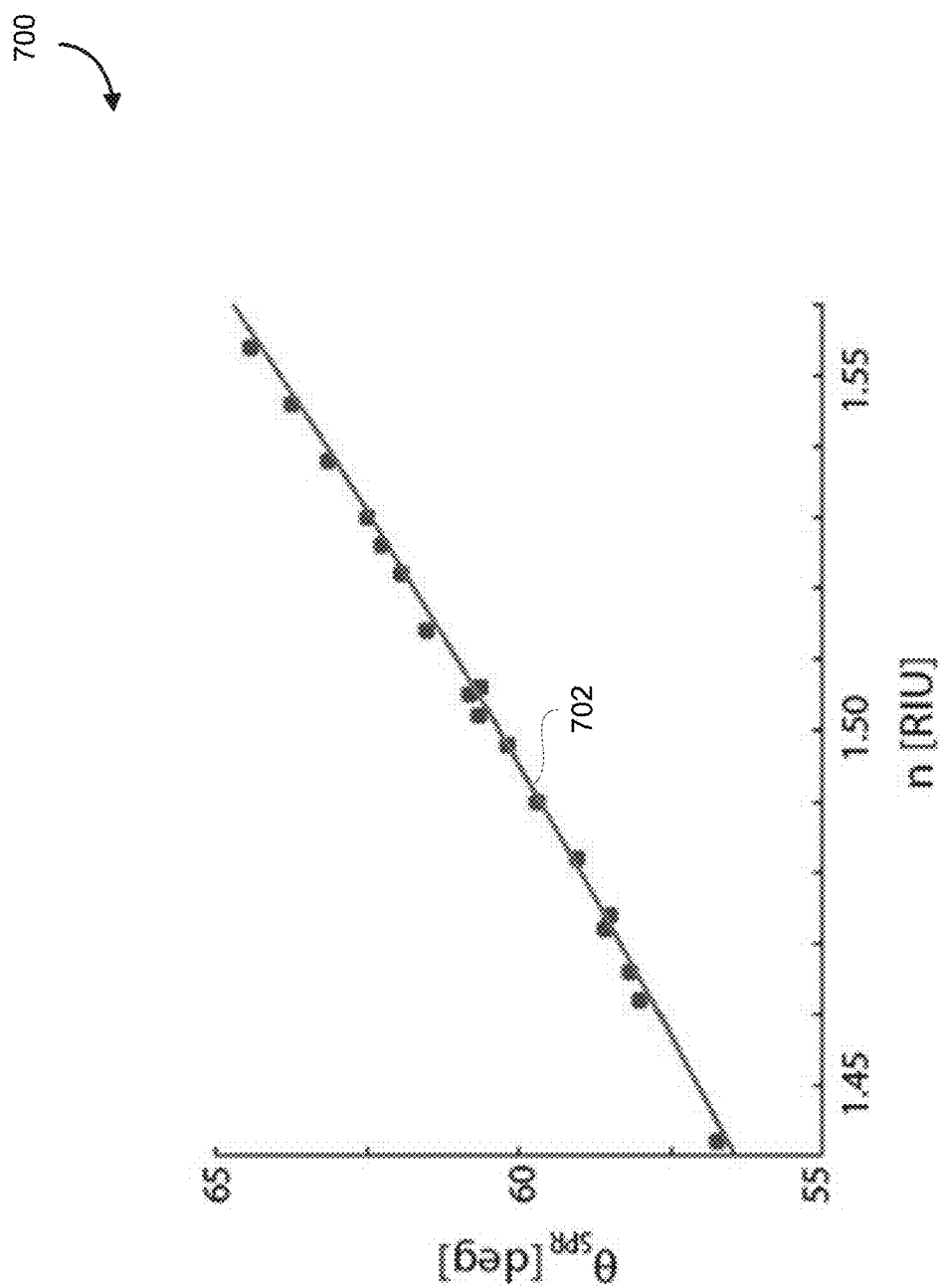
FIG. 7 provides an X-Y graph depicting the relationship between $\theta_{spr}$ and refractive index for the materials tested for both experimental (indicated by points) and theoretical data (indicated by the solid line), with the n, in refractive index units on the X axis, and the angle of resonance on the Y axis, according to some embodiments.

FIG. 7 provides an X-Y graph 700 depicting the relationship between $\theta_{spr}$ and refractive index for the samples tested for both experimental and theoretical data, with the n, in refractive index units on the X axis, and the angle of resonance on the Y axis, according to some embodiments. 702 is a line of best fit. Also shown on FIG. 7 is a theoretical curve based on a three layer Fresnel model using the refractive index of gold.

There appears to be strong agreement between the theoretical model and the experimental data. The non-linear response of over the range of detection required for oil and dilution differentiation can be compensated for by using a second order polynomial fit which gives an $R^2$ value of 0.9999 to the theoretical data and 0.9986 to the experimental data.

Referring to FIG. 8, FIG. 8 the X axis may be indicative of the angle of the incident beam, and the Y axis may be indicative of the reflectance (%/100).

In FIG. 8, the ratio of the power of the output light to the input light is shown as a function of the incident angle. The minimum value on each curve may correspond to the SPR angle (the angle of resonance). FIG. 8 provides results corresponding to eight different oil materials with different density (degree API). The sensitivity analysis may demonstrate an ability to differentiate oils with 1 API degree density difference.

Example Method

The following section provides some example steps that may be utilized for measuring characteristics of an oil material, according to some embodiments. Other, additional, less, and/or modified steps may be included as the steps provided solely as examples.

Step 1

Measure Reflected Power as a Function of Angles (See Scan Procedure Below)

1. Laser beam emitted from laser
   a. Laser light may be employed to limit the wavelength range of interrogation—lasers generate light with a very narrow range of wavelengths.
   b. A laser line filter may be added to decrease the range of wavelengths even further.
      i. For example, a laser used may have a central wavelength of 1550 nm with a min and max wavelength of 1520 nm and 1580, and a laser line filter with a gap of 5-10 nm centered at 1550 nm may help reduce the range of wavelengths to 1540-1560 nm, decreasing the error.
   c. Infrared wavelengths may be chosen as the oil material may be less absorbing in this region.

Figure 10:
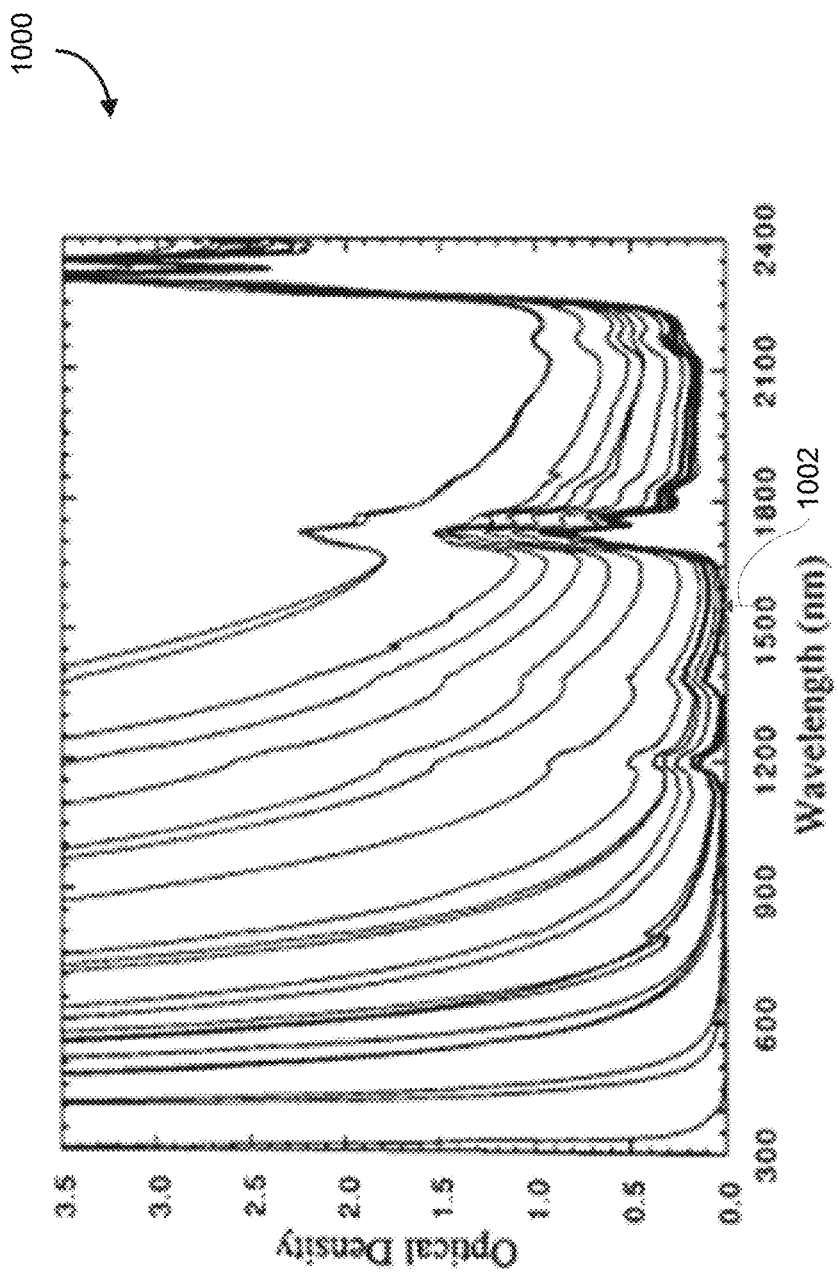
FIG. 10 provides a graph depicting the optical absorption spectra of oil materials.

FIG. 10 is a graph 1000 depicting the optical absorption spectra of oil materials, according to some embodiments, provided by Mullins, O., Mitra-Kirtley, S., & Zhu, Y. (1992). The electronic absorption edge of petroleum. Applied Spectroscopy, 46(9), 1405-1411.

The arrow 1002 points to 1550 nm where the absorption (optical density) for all the crude oils approaches a minimum. As wavelengths decrease the ashphaltene absorption begins to dominate. This high absorption could indicate that less light would be available for detection and consequently the minimum angle (i.e., resonance angle) more difficult to distinguish. By selecting an interrogation wavelength that is in the infrared frequency spectrum, drops in reflected power can more accurately be attributed to SPR as opposed to absorption.

2. A laser beam may be passed through a pinhole aperture used to select a central part of the beam. The addition of the pinhole aperture, in some embodiments, may aid in reducing diverging portions of the beam and may help increase the accuracy of the resonant angle and the sharpness of the SPR resonance.

Figure 11:
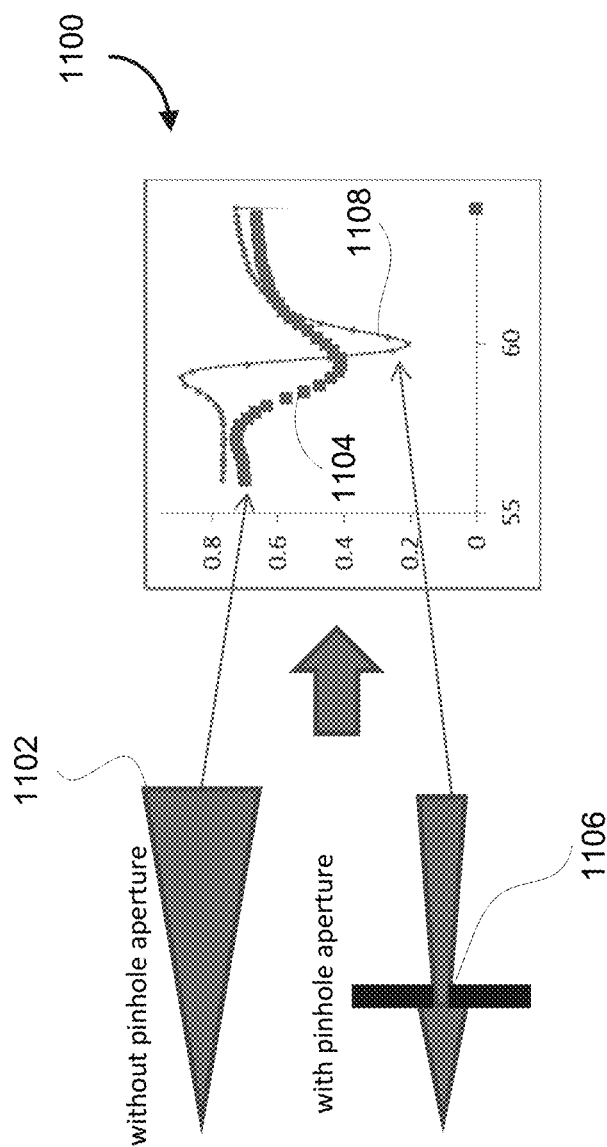
FIG. 11 provides a graph depicting two sets of measurements, one taken with a pinhole aperture, and one taken without a pinhole aperture, according to some embodiments.

FIG. 11 is a graph depicting two sets of measurements 1104 and 1008, one taken with a pinhole aperture 1106, and one taken without a pinhole aperture 1102, according to some embodiments.

3. The laser beam may be directed towards the oil material, and
   a. the laser beam is deflected by a turning mirror to hit the sample at a known angle;
   b. the laser beam source rotated about the sample; or
   c. the sample itself rotated while the beam is held stationary.
4. The laser beam is reflected off the sample and the intensity of the reflected beam is measured by a photodiode.
   a. This photodiode can be located near the sample in a down-hole application and may be pre-calibrated so that its temperature response is known;
   b. the photodiode can be cooled using electronic cooling (Peltier cooling) to reduce signal noise in high temperature environments; and/or
   c. the reflected beam can be collected by a fiber optic which returns the signal to a monitoring station where the reflected power can be measured under a controlled environment so that the photodiode are not affected by the environment in which the sensor is operating.
5. The intensity of the output signal is recorded by a computer.
6. The beam angle is then adjusted to a new angle.
7. Based on where the minimum reflectance occurred in the course scan, subsequent scans may be performed near this area and steps 1-6 repeated. This procedure can be automated using computer aided techniques. The entire range of the sensor can be analyzed by covering the full range of angles initially, and there may be additional scanning to provide higher accuracy in the region of interest as the resonant angle is iteratively determined. This approach may provide a broad detection range and faster processing times than if all angles were measured with the smallest possible angle iteration.

Figure 12:
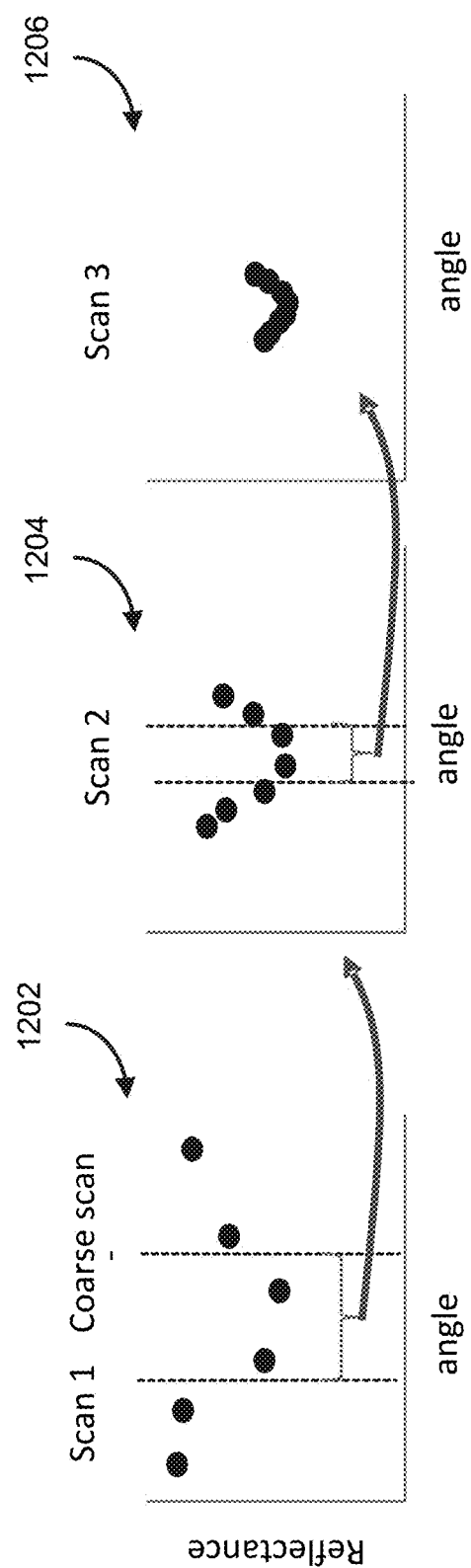
FIG. 12 contains a series of sample graphs where progressively smaller angles of interest are measured, according to some embodiments.

FIG. 12 contains a series of sample graphs 1202, 1204, and 1206 where progressively smaller angles of interest are measured, according to some embodiments. 1202 is representative of a coarse scan, and 1204 is representative of a finer scan, and 1206 is representative of an even finer scan.

Step 2

Figure 13:
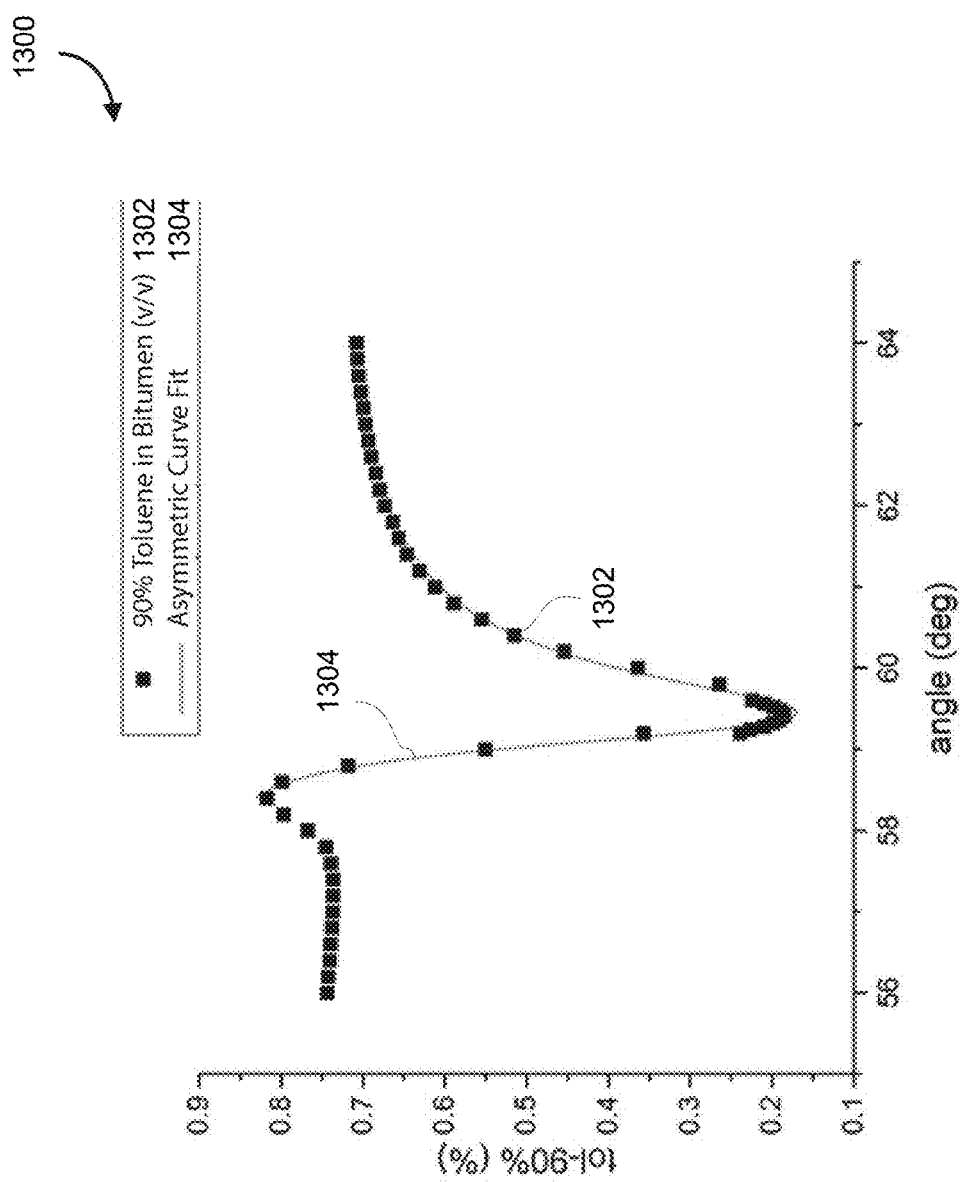
FIG. 13 provides a sample graph depicting results obtained for an oil material having toluene as a solvent, according to some embodiments.

An asymmetric curve may be fit through the measurements, and a minimum reflectance power may be located that may correspond to the SPR resonance angle. In some embodiments, a method described by Kurihara, 2002, may be utilized. FIG. 13 is a sample graph 1300 depicting results obtained for an oil material having toluene as a solvent, according to some embodiments. 1302 are measurements based on an oil material having 90% toluene, and 1304 is a line of best fit.

1. The SPR curve equation applied may be R=A*(1−(B+C*(x−D))/((x−D)^2+E^2)) where A, B, C, D, E are the fitting parameters and x is the beam angle and R is the reflectance.
2. Using suitable curve fitting software (such as Origin Lab), the best optimal values for the fitting parameters can be determined.
3. The minimum value of the fitted curve can be determined from the fitted function.
4. The standard error of the fitted curve to the data can be determined and used as a measure of the quality of the reflectance data collected, giving the user an indication of the reliability of a given measurement.

Step 3
Determine the Refractive Index of the Material Using SPR Model

Figure 14:
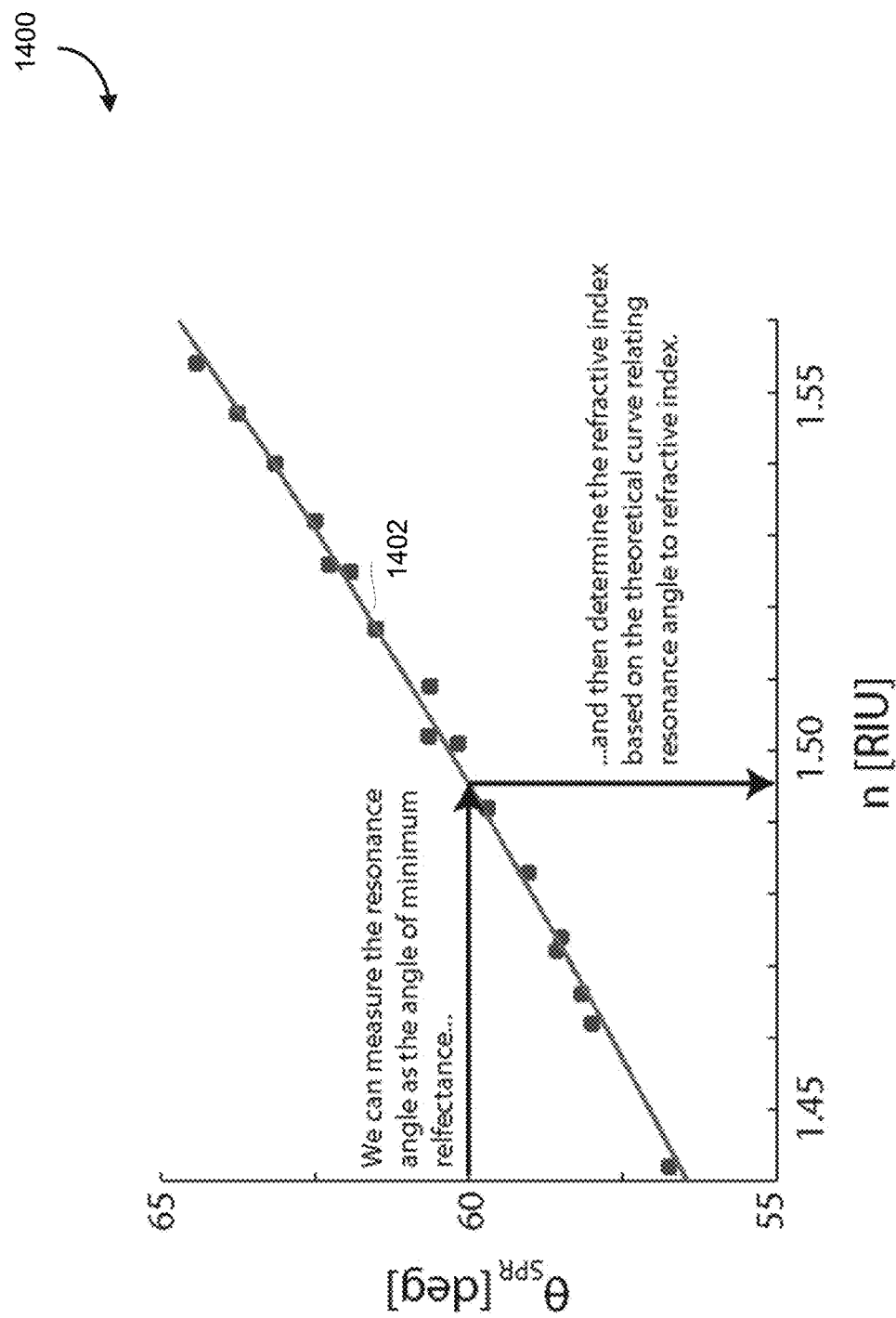
FIG. 14 provides a graph plotting resonant angles measured to refractive indices for various SPR apparatuses, according to some embodiments.

FIG. 14 is a graph plotting resonant angles measured to refractive indices for various SPR apparatuses, according to some embodiments. During sensor calibration, a best fit approximation 1402 of the resonant angle to refractive index relationship is calculated (red line in FIG. 14).

1. This red line may be based on an N-layer refractive index model. There may be additional steps that may be performed in relation to calibration based on the temperature of the sensor.
   a. The refractive index of gold (calibration may include the use of a lookup table or analytical expression for how this refractive index changes with respect to temperature).
   b. The refractive index of the prism (calibration may include the use of a lookup table or analytical expression for how this refractive index changes with respect to temperature) The temperature dependence of the refractive index for the glass prism can be found using the formula below. The values for the coefficients may be provided by a supplier for each of their glass types.

Constants of the Formula dn/dT
The temperature dependence of the refractive index can be calculated using the following formula:

$$\frac{dn_{abs}(\lambda, T)}{dT} = \frac{n^2(\lambda, T_0) - 1}{2n(\lambda, T_0)} \left( D_0 + 2D_1\Delta T + 3D_2\Delta T^2 + \frac{E_0 + 2E_1\Delta T}{\lambda^2 - \lambda_{TK}^2} \right)$$

The constants are valid for a temperature range from −100° C. to +140° C. and a wavelength range from 0.365 μm to 1.014 μm. The temperature coefficients in the data sheets are guideline values.

Temperature Coefficient of Refraction
$\Delta n_{nl}/\Delta T$ referring to air at normal pressure 1013.3 mbar
$\Delta n_{abs}/\Delta T$ referring to vacuum
   c. Gold film thickness—can be measured and certified during fabrication of the sensor.
2. This calibration data may be stored in a computer lookup table for faster processing.
3. Based on the resonant angle determined in STEP 2, the corresponding refractive index of the unknown fluid can be determined using the calibration look-up table. This can be done automatically by a computer algorithm Step 4
Estimate Additional Thermodynamic Properties of the Fluid Given the Refractive Index The refractive index can be used to determine input parameters for Equation of States (EOS), which provides various relationships between pressure, temperature and the molar volume of a fluid. For example considering the Redlich-Kwong EOS equation 1 from FIG. 15, the parameter b, the volume correction parameter, can be calculated using the refractive index. FIG. 15 provides a table of equations 1500 that may be applied in determining various parameters.

Referring to equation 8 from FIG. 15, a measured refractive index (n) can be put in this equation to calculate the parameter I which itself can be placed in equation 7 to calculate the $R_m$, etc. to calculate the parameter b which then can be plugged in the EOS, which is provided at equation 1. FIG. 16 is a table of variables 1600 that may be used in the equations of FIG. 15 and their descriptions.

The refractive index can also be used to determine other properties, such as viscosity, thermal conductivity and molecular diffusivity, for example, through the general relationship as defined by $$\theta = A\left(\frac{1}{I} - 1\right) + B, \left(\theta \text{ can be } \frac{1}{\mu}, \frac{1}{k}, D\right),$$

in which I is the refractive index parameter, A and B are various constants.

Applications
The following section describes potential applications that may be practiced in regards to some embodiments of the invention. There may be other, different, modifications, etc. of the below potential applications, and it should be understood that the description is provided as non-limiting, illustrative examples only. For example, there may be additions, omissions, modifications, and other applications may be considered.

The device 100 may be configured for testing in a variety of environments, such as in laboratory, with isolated samples, and/or in downhole in situ environments. Where the device 100 may be configured for downhole in situ experiments, the device 100 may be utilized in conjunction with other types of apparatus to position the device 100 downhole and/or to retrieve oil samples 102 for use with the device.

Figure 9:
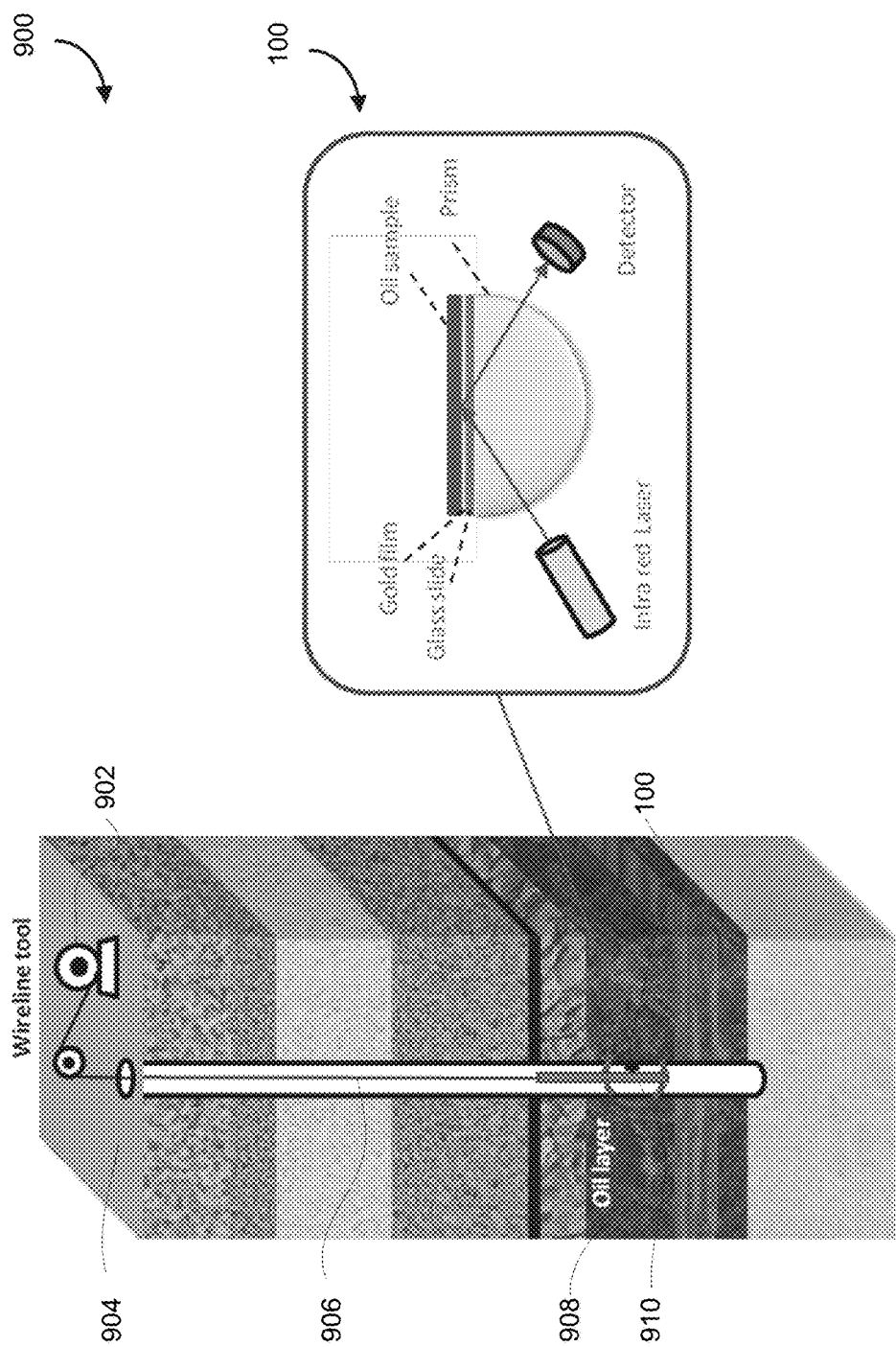
FIG. 9 may illustrate a sample wireline tool, wherein the device is lowered into a well, according to some embodiments.

Referring to FIG. 9, FIG. 9 may illustrate a sample wireline tool 900, wherein the device 100 is lowered into a well, according to some embodiments. A wireline apparatus 902 is used to operatively lower a housing 910 coupled to the device 100 below a surface 904, the device 100 being suspended on line 906, and may be lowered to a depth where an oil layer 908 exists.

The housing 910 may have an analytical platform having various sensors and mechanisms. Upon lowering of the housing 910, device 100 may be able to obtain or otherwise interact with a sample of oil layer 908 (e.g., to determine properties of the oil materials contained within the oil layer 908).

In some embodiments, device 100 may capture a sample of oil material for analysis. In some embodiments, device 100 may interoperate directly on the oil material. In some embodiments, a pinhole aperture may be utilized.

The wireline tool 900 and the device 100 may be configured for adaptation to various aspects of the downhole environment, such as increased pressure, temperature, pressure differentials, etc. For example, a device 100 may need to be ruggedized and/or have components suitably selected in the context of the environment it operates in. These factors may, for example, impact the practical dimensions of various components of the device 100, such as prism dimensions, conductive materials available, etc. There may, in some examples, be various coatings applied to the device 100 for increased reliability in downhole environments.

Variants

While angle interrogation is described in some embodiments of the above description, it should be understood that there may be other types of interrogation and/or techniques utilized in the identification and/or classification of various oil materials.

For example, wavelength interrogation techniques may be utilized, such as techniques described in U.S. Pat. No. 8,462,344 and U.S. Publication No. 20120105856.

General

The present system and method may be practiced with and/or controlled by computer devices including a desktop computer, laptop computer, tablet computer or wireless handheld. The present system and method may also be implemented with a computer-readable/useable medium that includes computer program code to enable one or more computer devices to implement each of the various process steps in a method in accordance with the present invention. In case of more than one computer devices performing the entire operation, the computer devices are networked to distribute the various steps of the operation. It is understood that the terms computer-readable medium or computer useable medium comprises one or more of any type of physical embodiment of the program code. In particular, the computer-readable/useable medium can comprise program code embodied on one or more portable storage articles of manufacture (e.g. an optical disc, a magnetic disk, a tape, etc.), on one or more data storage portioned of a computing device, such as memory associated with a computer and/or a storage system.

The functionality described may be implemented to any mobile platform, including the iOS™ platform, ANDROID™, WINDOWS™ or BLACKBERRY™.

It will be appreciated by those skilled in the art that other variations of the embodiments described herein may also be practiced without departing from the scope of the invention. Other modifications are therefore possible.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included.

Except to the extent explicitly stated or inherent within the processes described, including any optional steps or components thereof, no required order, sequence, or combination is intended or implied. As will be understood by those skilled in the relevant arts, with respect to both processes and any systems, devices, etc., described herein, a wide range of variations is possible, and even advantageous, in various circumstances.

What is claimed is:

1. A method of determining a refractive index of oil comprising:
    generating an incident beam, incident on a conductive material having one or more channels, and at an angle of incidence to the conductive material, between the conductive material and an oil material;
    separating the oil material, using the one or more channels, into separate phases;
    monitoring the power of a reflected beam;
    determining a refractive index of the separate phases of the oil material using at least the power of the reflected beam; and
    determining one or more other thermophysical values.

2. The method of claim 1, further comprising determining an angle of resonance by changing the angle of incidence of the incident beam; and wherein determining a refractive index of the oil material includes using at least the angle of resonance.

3. The method of claim 1 wherein the conductive material is a thin conductive film.

4. The method of claim 3 wherein the conductive material is a thin gold film.

5. The method of claim 1 wherein the conductive material is deposited in a Kretschmann configuration.

6. The method of claim 1 wherein a laser diode module generates the incident beam.

7. The method of claim 6 wherein the laser diode module is a polarized 4.5 mW laser diode module.

8. The method of claim 1 comprising determining at least one of oil type and quality based on the refractive index, the one or more thermophysical values or both.

9. The method of claim 1 comprising classifying the oil material using at least the refractive index of the oil material.

10. The method of claim 9 wherein the classifying of the oil material includes detecting at least two of oil, gas and brine phases.

11. The method of claim 1, wherein the separating of the oil material into the separate phases includes separating the oil material into at least two phases chosen from an oil phase, a brine phase, and a gas phase.

12. The method of claim 1, wherein the incident beam has a wavelength at which the oil material exhibits low absorption.

13. The method of claim 1, wherein the wavelength is an infrared wavelength.

14. The method of claim 1, further comprising reducing diverging portions of the incident beam.

15. The method of claim 12, further comprising refracting the incident beam using a refractor having a refractive index of at least the refractive index of the oil material at the wavelength at which the oil material exhibits low absorption.

16. The method of claim 11, wherein the determining of the refractive index of the oil material is effected on unseparated and separated oil material.

17. An apparatus for determining a refractive index of an oil material comprising:
    a light source for generating an incident beam;
    an incident beam refractor;
    a conductive material;
    a detector configured for sensing characteristics of a reflected beam; and an oil material receptacle configured for co-operatively disposing the oil material relative to the conductive material, the oil material interacting with the conductive material such that when the incident beam interacts with the conductive material under resonant conditions, the detector senses an attenuation in the power of the reflected beam, wherein the oil material receptacle includes one or more channels.

18. The apparatus of claim 17, wherein the light source is configured such that the incident angle of the incident beam is able to vary across a range of incident angles.

19. The apparatus of claim 18, comprising one or more micrometer arms operable to cause changes in the incident angle of the incident beam.

20. The apparatus of claim 18, comprising one or more micrometer arms controllable to automatically change the angle of the incident angle of the incident beam across a predetermined range of angles.

21. The apparatus of claim 19, wherein the micrometer arms are operable to cause changes in increments of approximately 0.2 degrees to identify regions of interest, and adjusted in increments of approximately 0.04 degrees in regions of interest.

22. The apparatus of claim 17, wherein the permissive material is made of materials having a refractive index of at least the refractive index of the oil material.

23. The apparatus of claim 17, wherein the conductive material is comprised of at least gold.

24. The apparatus of claim 17, wherein the conductive material has a thickness of 50 nm.

25. The apparatus of claim 17, wherein the permissive material and the conductive material are configured in an Otto configuration.

26. The apparatus of claim 17, wherein the incident beam has a wavelength at which the oil material exhibits low absorption.

27. The tool of claim 26, wherein the permissive material is made of materials having a refractive index of at least the refractive index of the oil material at the wavelength at which the oil material exhibits low absorption.

28. The apparatus of claim 17, further comprising an incident beam divergence reducer.

29. The apparatus of claim 17, wherein the one or more channels comprise separation channels that are configured to separate the oil material into at least two phases chosen from an oil phase, a brine phase, and a gas phase.

30. The apparatus of claim 17, wherein the one or more channels comprise separation channels that are configured to remove impurities from the oil material.

31. The tool of claim 17, wherein the oil receptacle includes a channeled portion including the one or more channels and a flat portion, wherein the light source and the detector are cooperatively configured to adjust the incident beam and reflected beam to compare the attenuation at the channeled portion and the flat portion.

32. A downhole tool adapted for determining a refractive index of an oil material in an oil-bearing portion of a formation, the downhole tool comprising:
a tool string configured to lower a housing into a wellbore disposed in the formation to a depth where the downhole tool interfaces with the oil-bearing portion; and
an analytical tool, coupled to the housing, the analytical tool including:
a light source for generating an incident beam;
an incident beam refractor; and
a conductive material, the conductive material including one or more channels; and
a detector configured for sensing characteristics of a reflected beam;
wherein the oil material is co-operatively disposed relative to the conductive material and the oil material interacts with the conductive material such that when the incident beam interacts with the conductive material under resonant conditions, the detector senses an attenuation in the power of the reflected beam.

33. The tool of claim 32, wherein the one or more channels comprise separation channels that are configured to separate the oil material into at least two phases chosen from an oil phase, a brine phase, and a gas phase.

34. The tool of claim 32, wherein the one or more channels comprise separation channels that are configured to remove impurities from the oil material.

35. The tool of claim 32, wherein the incident beam has a wavelength at which the oil material exhibits low absorption.

36. The tool of claim 35, wherein the permissive material is made of materials having a refractive index of at least the refractive index of the oil material at the wavelength at which the oil material exhibits low absorption.

37. The tool of claim 32, wherein the detector is located uphole of the conductive material and the light source, and the tool further comprises a fiber optic for transmitting the reflected beam the detector.

38. The tool of claim 32, further comprising an incident beam divergence reducer.

39. The tool of claim 32, wherein the conductive material includes a channeled portion including the one or more channels and a flat portion, wherein the light source and the detector are cooperatively configured to adjust the incident beam and reflected beam to compare the attenuation at the channeled portion and the flat portion.

* * * * *